(12) United States Patent
Asghar et al.

(10) Patent No.: US 6,221,887 B1
(45) Date of Patent: Apr. 24, 2001

(54) TREATMENT OF INFLAMMATORY DISORDERS WITH NMDA ANTAGONISTS AND SODIUM CHANNEL ANTAGONISTS

(75) Inventors: Aziz Asghar; Anne King, both of West Yorkshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/380,988

(22) PCT Filed: Apr. 28, 1999

(86) PCT No.: PCT/SE99/00701

§ 371 Date: Feb. 7, 2000

§ 102(e) Date: Feb. 7, 2000

(87) PCT Pub. No.: WO99/55322

PCT Pub. Date: Nov. 4, 1999

(30) Foreign Application Priority Data

Apr. 28, 1998 (SE) .................................................. 9801494

(51) Int. Cl.[7] ........................... A61K 31/44; A61K 31/16; A61K 31/135

(52) U.S. Cl. ........................ 514/357; 514/626; 514/649

(58) Field of Search .................................... 514/357, 626, 514/649

(56) References Cited

U.S. PATENT DOCUMENTS

| 5,538,993 | 7/1996 | Mechoulam et al. . |
| 5,635,530 | 6/1997 | Mechoulam et al. . |

FOREIGN PATENT DOCUMENTS

| 0615749 | 9/1994 | (EP) . |
| 9322279 | 11/1993 | (WO) . |
| 9714415 | 4/1997 | (WO) . |

Primary Examiner—William R. A. Jarvis
(74) Attorney, Agent, or Firm—White & Case LLP

(57) ABSTRACT

The invention relates to the use of certain pharmaceutical compounds as anti-inflammatory agents.

5 Claims, No Drawings

TREATMENT OF INFLAMMATORY DISORDERS WITH NMDA ANTAGONISTS AND SODIUM CHANNEL ANTAGONISTS

This application is a 317 of PCT/SE99/00701, filed Apr. 28, 1999.

The present invention relates to the use of certain pharmaceutical compounds as anti-inflammatory agents.

Compounds having NMDA (N-methyl-D-aspartate) antagonist activity are known in the art, for example see Watkins et al., Trends in Pharmacological Science, 11:25, 1990.

In particular certain compounds are disclosed in EPA 279937 as having NMDA antagonist activity and are useful for treating various CNS disorders such as epilepsy and Parkinson's disease. In particular the compound known as remacemide is known from EPA 279937 as an NMDA antagonist and has also been shown to act as a sodium channel antagonist (Wamil et al., Epilepsy Research 23:1. 1996). NMDA antagonists are also disclosed in U.S. Pat. Nos. 5,635,530 and 5,538,993 and are said to be useful as, inter alia, anti-inflammatory agents. It has now surprisingly been found that the compound remacemide and a metabolite of remacemide has activity in the carrageenan-induced inflammation model in the rat hindlimb. As a result it is expected that compounds having NMDA antagonist activity and/or sodium channel antagonist activity will be useful for the treatment of inflammatory disorders.

In a first aspect the invention therefore provides the use of an NMDA antagonist and/or sodium channel antagonist for the treatment of inflammatory disorders.

The term "an NMDA antagonist and/or sodium channel antagonist" means a single compound having both activities, a single compound having sodium channel antagonist activity, or, as used herein, two separate compounds each having one of the activities, that is a compound having NMDA antagonist activity and another compound having sodium channel antagonist activity. In the case of two separate compounds, these can be administered simultaneously or sequentially, that is separately, preferably less than 24 hours apart for example less than 12 hours apart and preferably less than one hour apart.

Suitable NMDA antagonists include those listed in WO 94/13295 such as a) channel blockers, i.e. antagonists which operate uncompetitively to block the NMDA receptor channel, b) receptor antagonists that compete with NMDA to act at the NMDA binding site, c) agents acting at either the glycine co-agonist site or any of the several modulation sites such as the zinc site, the magnesium site, the redox modulatory site, or the polyamine site, d) agents which inhibit the downstream effects of NMDA receptor stimulation such as agents which inhibit the activation of protein kinase C activation by NMDA stimulation, antioxidants, and agents that decrease phosphatidylinositol metabolism. Particular NMDA antagonists useful in the invention include those disclosed by Watkins et al., Trends in Pharmacological Science, 11:25, 1990.

Suitable sodium channel antagonists include those compounds disclosed by Taylor and Meldrum, Trends in Pharmacological Science, 16:309. 1995.

Examples of preferred compounds include Memantine (Merz); Riluzole (RPR); Lamotrigine; (GlaxoWellcome); Phenytoin and Phosphenltoin (Warner-Lambert), Carbamzezepine and Oxcarbamazepine (Novartis); Remacemide and (S)-1-phenyl-2-(2-pyridyl)ethanamine.

Particularly suitable compounds include those disclosed in EP 279937 and EP 633 879.

Preferred compounds of the invention include compounds of formula (I):

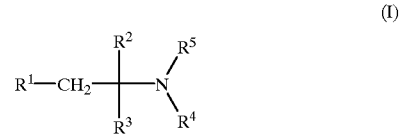

where:
R$^1$ is pyridyl, phenyl or 4-fluorophenyl;
R$^2$ is phenyl or 4-fluorophenyl;
R$^3$ is hydrogen, C$_{1-6}$ alkyl or methoxycarbonyl;
R$^4$ is hydrogen or methyl; and
R$^5$ is hydrogen or COCH$_2$NH$_2$, and metabolites thereof both as free base and pharmaceutically acceptable salts thereof.

Preferably the compound of formula (I) is 1-phenyl-2-(2-pyridyl)ethanamine or a pharmaceutically acceptable salt thereof (preferably the (S) isomer), or 2-amino-N-(1,2-diphenyl-1-methylethyl)acetamide (remacemide) or apharmaceutically acceptable salt or metabolite thereof. Preferred metabolites of remacemide include the compound known as 2,3-diphenyl-2-propylamine or a pharmaceutically acceptable salt thereof which has the following structure:

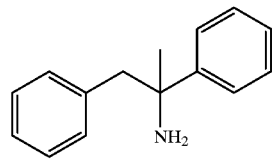

Suitable salts include all known pharmaceutically acceptable salts mentioned in EP 279937 and EP 633 879 such as acid addition salts and preferably hydrochloride salts.

The invention also provides a method of treating or preventing inflammatory disorders which comprises administering to a patient a compound having NMDA antagonist activity and/or sodium channel antagonist activity or a pharmaceutically acceptable salt thereof.

Particular inflammatory disorders which can be treated include arthritic conditions, eczema, psoriasis, dermatitis and other inflammatory conditions such as sunburn; inflammatory eye conditions such as uveitis and conjunctivitis; lung disorders in which inflammation is involved such as asthma and bronchitis; conditions of the GI tract including aphthous ulcers, gingivitis, Crohn's disease, atrophic gastritis, gastritis varialoforme, ulcerative colitis, coeliac disease, regional ileitis, peptic ulceration, pyresis, pain and other damage to the GI tract, for example damage from infections by, for example, Helicobacter pylori, or treatments with non-steroidal anti-inflammatory drugs.

In a further aspect the invention provides the use of a compound having NMDA antagonist activity and/or sodium channel antagonist activity for the treatment of inflammatory induced pain, in particular fibromyalgia. Preferred compounds are those given above, particularly remacemide.

In a further aspect the invention provides a compound having NMDA antagonist activity and/or sodium channel antagonist activity, in particular a compound of formula I or a metabolite thereof, in the manufacture of a medicament for use in the prevention or treatment of inflammatory disorders.

The invention also provides a compound having NMDA antagonist activity and/or sodium channel antagonist activity for the treatment or prophylaxis of inflammatory disorders Suitable daily dose ranges are from about 1.0 mg/kg to about 100 mg/kg. Unit doses may be administered conventionally once or more than once a day, for example, 2, 3, or 4 times a day, more usually 1 or 2 times a day.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration, all of which are well known in the art.

The following example illustrates the invention.

EXAMPLE 1

An inflammatory response was elicited in 12–13 day old Wistar rats by injection of 50 ul of carrageenan (0.5% in sterile physiological saline into the right footpad under brief halothane anaesthesia). Paw oedema, a measure of the inflammation produced, was assessed by measuring dorsal-plantar thickness of both hind paws, using vernier calipers. A difference score was generated by subtraction of the value for the non-injected paw from that for the injected paw in each animal. Three baseline readings were taken at 90 min, 60 min and 30 min before application of test compounds. Measurements were made at 30 min, 1hr and thereafter at intervals of 1hr up to 6hr after carageenan application.

2,3-diphenyl-2-propylamine, dissolved in sterile physiological saline (0.9% NaCl w/v), was administered in a dose of 75 mg/kg to six animals by intraperitoneal (i.p.) injection 30 min prior to carrageenan injection. Control animals (n=6) received intraperitoneal injections of vehicle alone, 30 min before injection of carrageenan.

Data were expressed as mean±SEM and plotted as a function of time. Statistical analysis was performed using an ANOVA analysis of the areas under the curves, followed in the case of significant difference (p<0.05) by student's unpaired t-test analysis at individual time points.

Intraplantar injection of carageenan resulted in the development of paw oedema, with a duration>6hr and which peaked at 4hr post application. Pretreatment with 2,3-diphenyl-2-propylamine, 75 mg/kg i.p. significantly (p<0.05) reduced the extent of paw oedema elicited at 2hr, 3hr and 4hr after carageenan treatment, compared with application of the drug vehicle alone.

What is claimed is:

1. A method of treating or preventing inflammatory disorders in a mammal in need thereof, which comprises administering to the mammal a compound having NMDA receptor antagonist activity or sodium channel antagonist activity or a metabolite and/or pharmaceutically acceptable salt thereof and wherein the compound is a compound of formula (I):

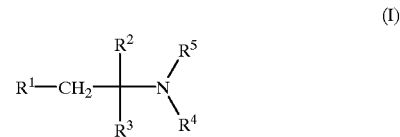

wherein
   $R^1$ is Pyridyl, phenyl or 4-fluorophenyl;
   $R^2$ is phenyl or 4-fluorophenyl;
   $R^3$ is hydrogen, $C_{1-6}$ alkyl or methoxycarbonyl;
   $R^4$ is hydrogen or methyl; and
   $R^5$ is hydrogen or $COCH_2NH_2$.

2. The method according to claim 1 wherein the compound of formula (I) is remacemide or a phanmaceutically acceptable salt and/or metabolite thereof.

3. The method according to claim 1 wherein the compound of formula (I) is 2,3-diphenyl-2-propylamine or a pharmaceutically acceptable salt thereof.

4. The method according to claim 1 wherein the compound of formula (I) is (S)-1-phenyl-2-(2-pyridyl)ethanamine or a pharmaceutically acceptable salt thereof.

5. The method according to any one of claims 1–4 wherein the inflammatory disorder is fibromyalgia.

* * * * *